US00RE37479B1

(19) United States
(12) Reissued Patent
Kuslich

(10) Patent Number: US RE37,479 E
(45) Date of Reissued Patent: Dec. 18, 2001

(54) SPINAL FIXATION DEVICE

(75) Inventor: Stephen D. Kuslich, Stillwater, MN (US)

(73) Assignee: Spineology, Inc., Stillwater, MN (US)

(21) Appl. No.: 09/227,163

(22) Filed: Jan. 7, 1999

Related U.S. Patent Documents

Reissue of:
(64) Patent No.: 5,591,235
Issued: Jan. 7, 1997
Appl. No.: 08/404,236
Filed: Mar. 15, 1995

(51) Int. Cl.[7] ..... A61F 2/44
(52) U.S. Cl. ..... 623/17.11; 606/61
(58) Field of Search ..... 623/16.11, 17.11, 623/18.11; 606/60, 61, 62, 63, 64, 69, 70, 71

(56) References Cited

U.S. PATENT DOCUMENTS

| | | | | |
|---|---|---|---|---|
| 4,059,115 | * | 11/1977 | Jumashev et al. | 606/82 |
| 4,289,123 | * | 9/1981 | Dunn | 606/61 |
| 4,448,191 | * | 5/1984 | Rodnyansky et al. | 606/61 |
| 4,658,809 | * | 4/1987 | Ulrich et al. | 606/61 |
| 4,743,260 | * | 5/1988 | Burton | 623/16.11 |
| 4,790,297 | * | 12/1988 | Luque | 606/61 |
| 4,805,602 | * | 2/1989 | Puno et al. | 606/61 |
| 4,834,757 | * | 5/1989 | Brantigan | 623/17 |
| 4,854,304 | * | 8/1989 | Zielke | 606/61 |
| 4,865,604 | * | 9/1989 | Rogozinski | 623/18 |
| 4,878,915 | * | 11/1989 | Brantigan | 623/17 |
| 4,892,545 | * | 1/1990 | Day et al. | 623/17 |
| 4,913,134 | * | 4/1990 | Luque | 606/61 |
| 5,007,909 | * | 4/1991 | Rogozinski | 606/61 |
| 5,015,247 | * | 5/1991 | Michelson | 606/61 |
| 5,015,255 | * | 5/1991 | Kuslich | 623/17 |
| 5,059,193 | * | 10/1991 | Kuslich | 606/61 |
| 5,102,412 | * | 4/1992 | Rogozinski | 606/61 |
| 5,129,388 | * | 7/1992 | Vignaud et al. | 606/61 |
| 5,171,279 | * | 12/1992 | Mathews | 623/17 |
| 5,181,917 | * | 1/1993 | Rogozinski | 606/61 |
| 5,242,443 | * | 9/1993 | Kambin | 606/60 |
| 5,242,446 | * | 9/1993 | Steffee et al. | 606/61 |
| 5,261,911 | * | 11/1993 | Carl | 606/61 |
| 5,261,913 | * | 11/1993 | Marnay | 606/61 |
| 5,360,431 | * | 11/1994 | Puno et al. | 606/61 |
| 5,364,399 | * | 11/1994 | Lowery et al. | 606/69 |
| 5,437,669 | * | 8/1995 | Yuan et al. | 606/61 |
| 5,466,237 | * | 11/1995 | Byrd, III et al. | 606/61 |
| 5,474,555 | * | 12/1995 | Puno et al. | 606/61 |
| 5,540,688 | * | 7/1996 | Navas | 606/61 |

FOREIGN PATENT DOCUMENTS

| | | | | |
|---|---|---|---|---|
| 4220218 | * | 12/1993 | (DE) | 623/17 |
| 2682280 | * | 4/1993 | (FR) | 606/61 |
| 9116020 | * | 10/1991 | (WO) | 606/61 |

* cited by examiner

*Primary Examiner*—Gene Mancene
*Assistant Examiner*—Eduardo C. Robert
(74) *Attorney, Agent, or Firm*—Vidas, Arrett & Steinkraus

(57) ABSTRACT

An spinal fixation device for stabilizing vertebrae. A hollow screw is inserted into a hole saw recess in each adjoining vertebrae. A channel is cut into the vertebrae into which a joining rod is inserted such that no part of the device protrudes above the bone. A locking cap is used to secure the rod to the screws.

14 Claims, 5 Drawing Sheets

SPINAL FIXATION DEVICE

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to a device for fixing adjacent vertebrae to each other using a rod and unique hollow screws.

2. Description of the Related Art

Fixation (or fusion) of vertebral columns with bone material or rods and plates is a common, long practiced surgical method for treating a variety of conditions. Many of the existing procedures involve components that protrude outwardly that may contact and damage a body part, such as the aorta, the vena cava, the sympathetic nerves, the intestine and the ureter. Also, many constructions involve components that may loosen and cause undesirable problems. A Dunn device was on the market until pulled by the U.S. Food & Drug Administration because of problems with delayed rupture of the aorta secondary to the device being so bulky as to contact the aorta, erode its surface and lead to fatal hemorrhage in several cases.

U.S. Pat. No. 5,152,303 issued to Allen on Oct. 6, 1992 relates to an anterolateral spinal fixation system including a cannulated screw threaded into a vertebra and a rod attached to the screw. The process involves threading the cannulated screw into a pilot hole drilled into the vertebral body portion and fastening a rod at its lower and upper ends to the vertebral body by the cannulated screws. (Col. 3, lines 62–64; Col. 4, lines 5–8).

U.S. Pat. No. 4,059,115 issued to Jamashev et al. on Nov. 22, 1977 relates to a surgical instrument for operation of anterior fenestrated spondylodesis in vertebral osteochondrosis. The instrument includes a hollow cylindrical cutter with a cutting edge, and a handle. By rotation of the handle accompanied with slight pressure the cutter is worked into the bodies of the adjacent vertebras (abstract, Col. 6, lines 56–58).

U.S. Pat. No. 5,015,247 issued to Michelson on May 14, 1991 relates to a method of performing internal stabilization of a spine. The method involves seating a drill sleeve into the two vertebrae and drilling the vertebrae with the drill installed through the drill sleeve. Bagby U.S. Pat. No. 4,501,269 is mentioned. (Col. 6, lines 27–30, Col. 7, line 68, Col. 9, lines 22–25, 39).

Current devices have substantial deficiencies when osteoporotic bone is encountered. The soft, decalcified bone in such patients has poor pull-out strength for screws. Bone screws are known to have very little holding power in osteoporotic bone and loosen readily, severely limiting the holding power and fixation ability of current devices.

Some devices have designs that include hollow screws or screws with transversely drilled holes, presumably to improve holding power and allow bone to grow therethrough. These devices are all relatively small screws which are not capable of large surface area fixation.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

The invention provides a method and device for fixing two or more vertebrae. The process is elegantly simple and solves many of the problems attendant with previous devices.

Each vertebra to be joined is prepared by forming a partial annular cut, as by a hole saw, preferably leaving the core plug of bone in place. A hollow screw is threaded into the annular ring recess thus formed. A channel is cut in the vertebral bone between each of the screws to accommodate a rod that is placed over each screw. A locking cap over each screw secures the rod to the screws and thereby fixes the spine as desired.

The method and device provide many advantages. The hollow screws are exceptionally strong, having greater holding surface area than conventional solid screws. The rod is held in the screw between two widely spaced slots. The rod is also held firmly by a third point by a dimple on the locking cap. The rod is secured to the screws by at least three points of fixation over a much greater distance than traditional systems. This provides a linkage which is significantly greater in terms of mechanical stability over the prior art.

Holes in the side walls of the hollow screws allow for bone ingrowth to further strengthen the connection. Since the bone plug is not removed, the screw's wall is very thin, bone can grow through the screw rapidly, thus securely fusing the screw to the vertebra and provides a better anchor to the vertebral bone. Additionally, as the bone grows through the holes in the screw, the bond becomes stronger with time. Prior art devices use screws that may slowly become less secure with age and the inevitable micromotion that occurs between the screw and the vertebral bone.

By varying the cross-section geometric structure and diameter of the rod, various degrees of stiffness may be imparted. Also, by varying the geometric cross-section structure of the rod, stiffness may be imparted selectively in the appropriate plane of motion. For instance, if increased flexion-extension stability is desired, the rod can be oriented in the flexion-extension plane and elongated such that it will provide greater stiffness in flexion-extension than in lateral bending. Such a feature will allow the surgeon to define the plane of stiffness necessary to match the pathology encountered.

The rods within the cut channels avoid the cantilever effect of prior art devices where the load is carried far from the center of the spine. Thus, the rod acts more like an intramedullary rod in the vertebrae. This is far preferable in that a rod nearer the center of the axis of rotation does not have the cantilever effect of prior art systems. This also presents no protrusions that may abut against vital body components.

The process is very simple, requiring only the drilling of a single hole saw cut in each vertebra, formation of channels therebetween and installation of the hollow screws, placement of the rod and securement with the locking caps.

BRIEF DESCRIPTION OF THE DRAWINGS

A detailed description of the invention is hereafter described with specific reference being made to the drawings in which.

DESCRIPTION OF THE PREFERRED EMBODIMENTS

Figure 1:
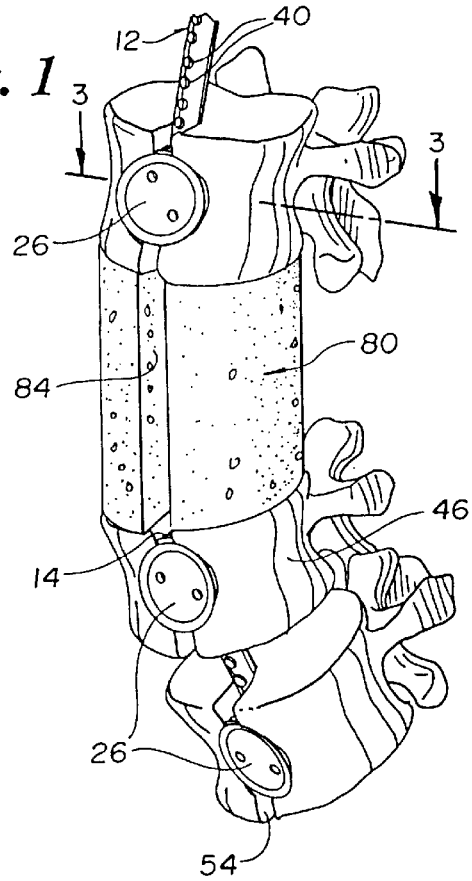
FIG. 1 is a perspective view of the device of the invention securing vertebrae together.
Figure 2:
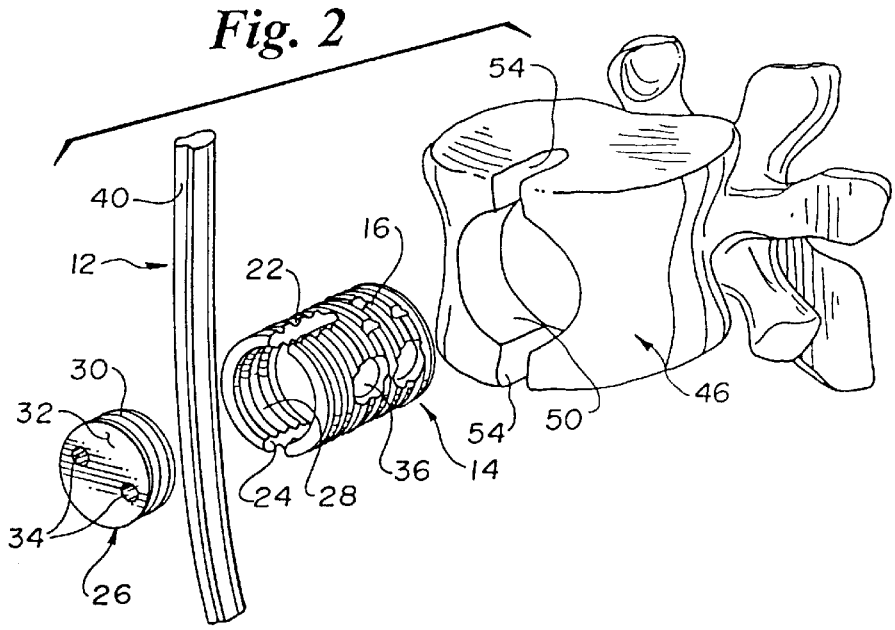
FIG. 2 is an exploded view of the rod, screw, cap and prepared vertebrae.

With specific reference to FIGS. 1 and 2 it will be seen that an anterior spinal fixation system 10 may join adjacent vertebrae together. The system includes an elongated rod 12 and at least two hollow cylindrical screws 14. Each screw 14 includes external bone engaging threads 16, internal cap engaging threads 28, an upper rim 18 and a lower rim 20. The internal threads 28 need only be as deep as the locking cap. A smooth inner wall is preferred to avoid placing torque on the remaining bone core during insertion of the screw. As shown in FIG. 2, upper rim 18 is broken by two opposing rod fixation slots 22, 24 that are sized such that rod 12 may pass into the slots 22, 24 as shown. Preferably, the screws 14 include a plurality of bone ingrowth openings 36 through the side walls which allow bone to grow therethrough.

The rod 12 is held to the screws by a locking cap 26. As shown, locking cap 26 may be disc-shaped, having threads 30 about the circular periphery. Top 32 of the cap 26 may have a pair of spaced holes 34 to which a tool (not shown) may connect to insert said cap 26 into a hollow, threaded screw 14. Cap 26 may be threaded into said screw 14 such that no part of said cap projects beyond the screw 14. The cap may be porous and may have holes to allow bone ingrowth and increase the blood supply to the interior.

Figure 6:
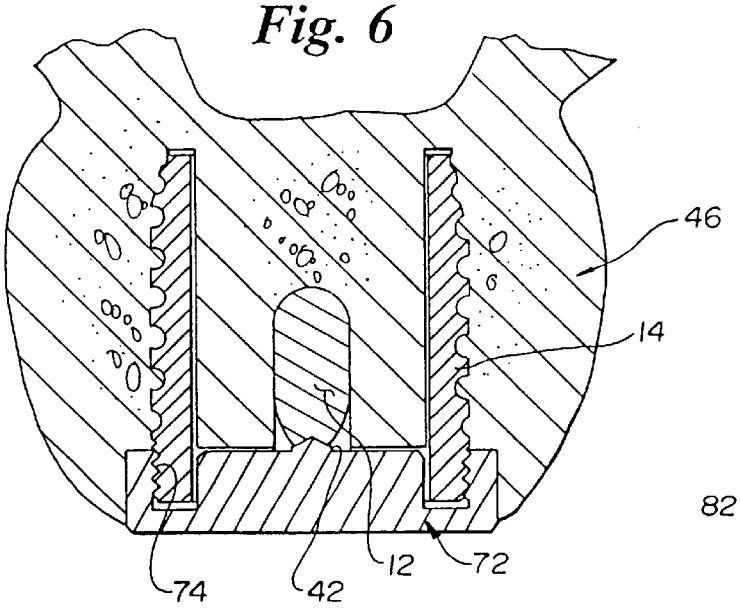
FIG. 6 is a cross-sectional view similar to FIG. 3 with an overcap design.

Alternatively, as shown in FIG. 6, the cap may be designed as an overcap 72 which engages with threads 74 on the outer surface of the bone screw 14. As shown, overcap 72 includes a cap projection 42 which abuts against rod 12. In the case of an overcap, some bone may be removed to accommodate the overcap as shown.

Rod 12 is preferably made of a biocompatible, malleable metal such as titanium. A rod of titanium has an advantage of having a modulus of elasticity similar to natural bone. In any case, the rod is bent by the surgeon to attain the correct configuration desired for the patient. As shown in the Figures, the rod 12 may have a plurality of spaced dimples 40 which may be round or elongated. The dimples 40 interface with a mating projection 42. In the case of a round dimple 40, the projection 42 engagement serves to prevent slippage of the rod relative to the screw 14. An elongated dimple 40 allows limited slippage which is sometimes desirable.

FIGS. 5a–e show that the cross-section of rod 12 may be nearly any shape other than round. Although a round cross-section rod would work, any non-round rod provides better torsion control. The size of the rod may be selected depending on the individual patient's size. As stated previously, the cross-sectional shape of the rod may be altered to provide stability in the proper axis of motion for a particular patient.

Figure 3:
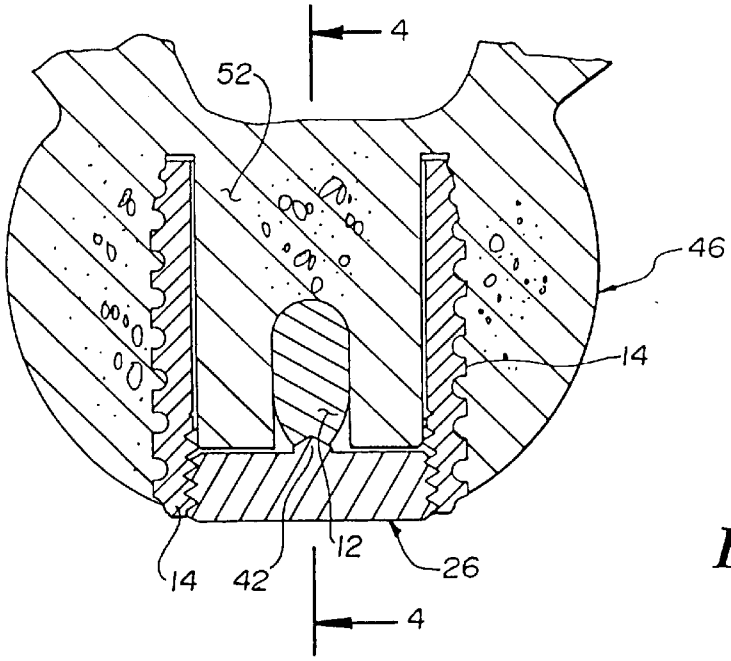
FIG. 3 is a cross-sectional view taken through line 3—3 of FIG. 1.
Figure 4:
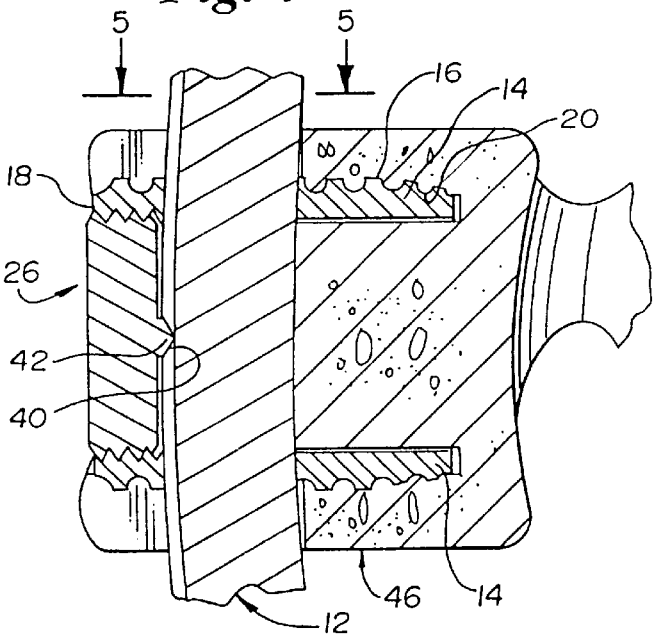
FIG. 4 is a cross-sectional view taken through line 4—4 of FIG. 3.
Figure 5A:
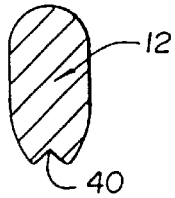
FIG. 5a is a cross-sectional view taken through line 5—5 of FIG. 4 showing the rod in cross-section.
Figure 5B:
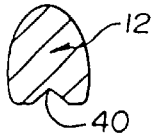
FIG. 5b is a cross-sectional view taken through line 5—5 of FIG. 4 showing an alternate rod in cross-section.
Figure 5C:
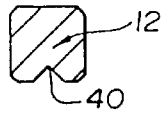
FIG. 5c is a cross-sectional view taken through line 5—5 of FIG. 4 showing an alternate rod in cross-section.
Figure 5D:
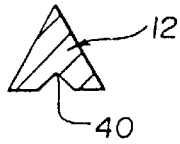
FIG. 5d is a cross-sectional view taken through line 5—5 of FIG. 4 showing an alternate rod in cross-section.
Figure 5E:
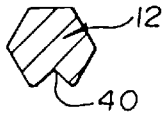
FIG. 5e is a cross-sectional view taken through line 5—5 of FIG. 4 showing an alternate rod in cross-section.

Installation of the device is straight forward. The surgeon exposes the vertebra 46 anteriorly and drills a cylindrical opening 50 in the vertebral bone as shown in FIG. 2. Preferably, a hole saw is used to form the opening 50, since a hole saw will leave the core 52 in place. For ease of illustration, FIG. 2 does not show a bone core 52, although the bone core 52 is shown in FIGS. 3 and 4. If a bone core 52 is not left in place, the opening may be packed with bone or bone substitute. It is noted that the bone opening 50 may be threaded if the drill used is self-tapping or it may be tapped by an additional tool used after drilling.

Preferably, the implant screws 14 are slightly larger in external diameter than the external diameter of the hole saw cut, thus providing a high friction secure linkage to the vertebral body. This also provides a screw with an internal diameter slightly larger than the outer diameter of the bone core, thus reducing the possibility of torquing the core during placement of the screw. Torquing the core in the process of insertion may destroy the blood supply to the core at its posterior surface. This would be undesirable since it may lead to delayed incorporation of the bone locking ability through the holes in the screw.

It may also be possible to use a bone screw 14 of the device to cut its own opening 50. In such a case, the screw 14 is then left in place after fully inserted.

Each of the vertebra adjacent another bone opening 50 is then cut, as by a chisel or router tool, to form a channel 54 of a depth to hold at least half the diameter of the rod 12. Although the vertebrae may be connected without the channel using the device and methods of this invention, many of the advantages are lost if at least most of the rod is not in a channel 54.

Figure 8:
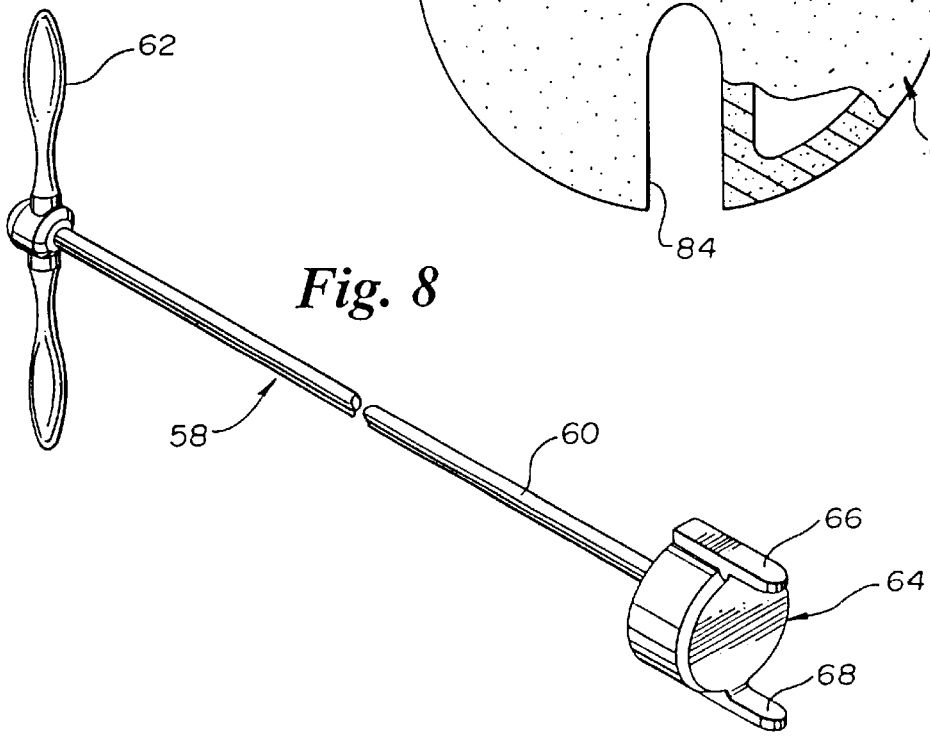
FIG. 8 is a tool for threading in the device into the annular ring recess in the vertebral body.
Figure 10:
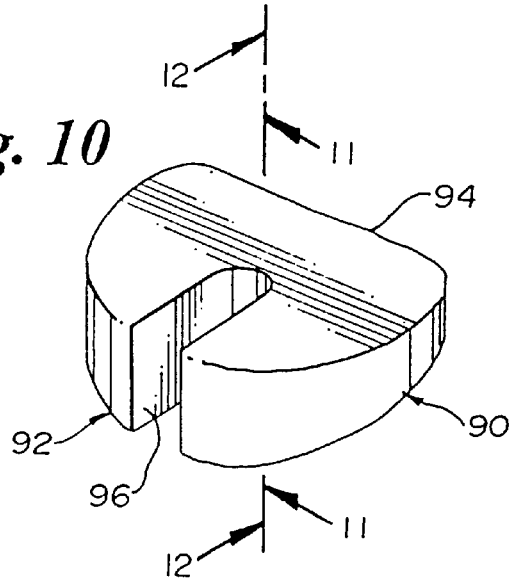
FIG. 10 is a perspective view of a wedge placable between adjacent vertebrae.
Figure 11:
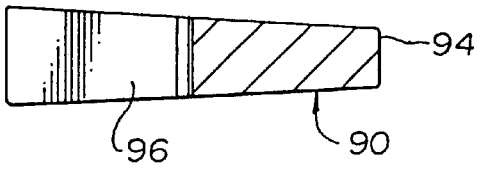
FIG. 11 is a cross-sectional view of the wedge of FIG. 10 through line 11—11.

The bone screws 14 are then screwed into the bone openings 50 with threads 28, 16 on the interior and exterior of the bone screws 14 engaging vertebral bone. The screws are positioned such that the rod fixation slots 22, 24 line up with the bone channels 54. A tool 58 as shown in FIG. 8 may be used to screw the bone screws 14 into bone openings 50.

As shown, tool 58 includes a shaft 60 with a handle 62 on one end a screw engaging head 64 on the other end. The screw engaging head 64 includes a pair of tabs 66, 68 that engage with slots 22, 24. The head 64 closely fits into the interior of the screw 14. No part of tool 58 projects beyond the outer circumference of the bone screws 14.

A rod 12 of the required length is then bent to the required shape and inserted into each screw via the rod fixation slots 22, 24 and into the formed bone channels 54. The rod 12 may be removed to adjust the curvature of the spine that will be defined by the installed system as needed. Once the degree of correction has been achieved, the rod is captively held in place by securing a locking cap 26 over each screw 14 thereby trapping the rod 12 in place.

The bone screws 14 are preferably placed into the vertebral bone quite deep, leaving a safety zone of about 3 mm. Depending on the size of the vertebrae, the screw diameters may range from 1.5 to 3.5 cm. Preferably, the diameter of the screws 14 is sufficient to cut into the harder, outer bone of the vertebra. The screws 14 may have a relatively thin cylindrical wall and still provide great strength and holding power.

The installed system of the invention provides a spinal correction with many important advantages. Since the cylindrical screws have far greater surface area than a conventional solid screw, the holding power is much higher. The installed system is entirely contained within the confines of the vertebral bone. Nothing projects outwardly that may contact adjacent body structures. The rod 12 is much closer to the center of the vertebral meaning that undesirable cantilever effects as in the prior art devices is greatly reduced.

The system of the invention may be used to stabilize many or only two vertebrae. It may be used to provide corrections due to rumor, fracture, degenerative disease, deformity or infection. The non-round rod used in most cases provides longitudinal rotational control. The normal healing process of the body will cause bone growth around the screws, rods and caps to lock the system even more securely to the vertebra. The screws 14 may include perforations throughout the length of the cylinder to allow bone ingrowth which may increase holding power.

Figure 9:
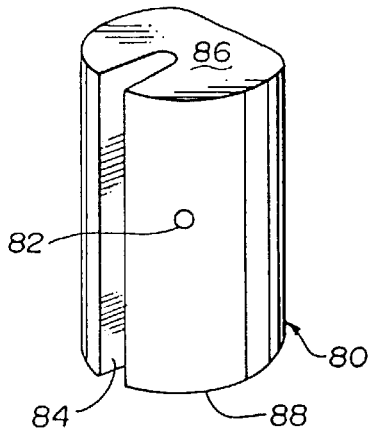
FIG. 9 is a perspective view of the corpectomy block of FIG. 7.
Figure 7:
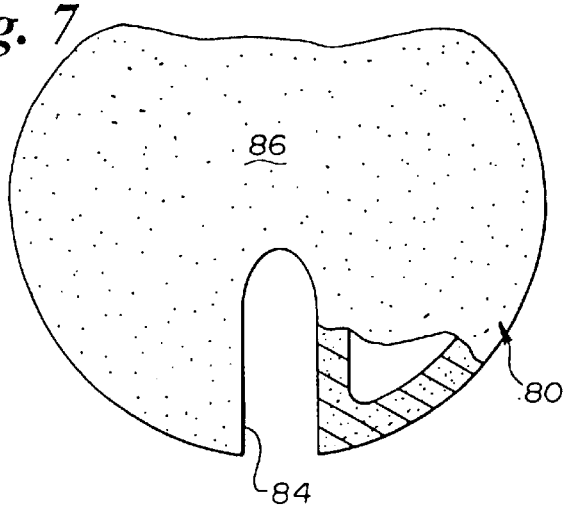
FIG. 7 is an end view of a corpectomy block partially cut away.

FIGS. 1, 7 and 9 show that the invention may be used between two or more adjacent vertebrae and may be used in conjunction with a corpectomy block 80 which functions as a spacer for a removed vertebral body. A corpectomy block 80 is used when a large portion of the vertebral body has been removed, such as to remove tumor, fractured bone or in cases of massive bone loss. Most of the vertebra is removed anteriorly forming a gap between the remaining vertebrae. The usual prior art solution is to provide a number of fill plates with rods or a large ceramic block anchored with plates and conventional screws. U.S. Pat. No. 5,192,327 shows a suitable corpectomy block which merely needs to be designed with a slot through which the rod 12 may pass.

In FIG. 7 and 9 are corpectomy block 80 is shown in which the block is substantially hollow and is formed from a body compatible material such as titanium or ceramic. The block may be porous or at least roughened at the ends to allow bone ingrowth. A fill port 82 may be built into the block 80 to allow addition of bone graft. The block 80 includes a lengthwise slot 84 through which rod 12 may pass. In use, a block 80 of the appropriate size is fitted between the remaining vertebrae after re-section and is filled with bone graft. The rod 12 is placed through the slot 84 and is tightened at each bone screw 14 by end caps 26 or 72. This firmly holds the corpectomy block 80 in place to allow bone fusion to the adjacent vertebrae as shown in FIG. 1.

The block should allow for vascular ingrowth by having at least porous end plates 86, 88. The block 80 may be porous titanium or a ceramic with roughened end plates.

FIG. 1 shows that the invention will function even if one or more vertebra are resected and replaced with a corpectomy block. In all forms of the invention, the hollow screws 14 provide greater holding power and allow for an intramedullary rod that eliminates the cantilevered structures found in prior art pedicle screw systems such as in U.S. Pat. No. 5,324,290 that issued Jun. 28, 1994. The present invention directs the forces from nearer the center of the vertebrae and therefor the axis of forces and motion.

In some cases, the spinal column is in need of realigning, front to back, side to side, or both. FIGS. 10 through 17 show means of correcting alignment while using the spinal fixation device 10 of the invention.

In FIGS. 10–13 wedges are shown which may be inserted between the vertebrae in place of a removed disc. The wedge 90 of FIGS. 10–12 may be a solid block of ceramic, may be a titanium wedge or any other body implantable material that could replace a disc. The anterior side 92 of wedge 90 is higher than the posterior edge 94. A slot 96 is formed to allow the rod 12 to pass thereby.

Figure 12:
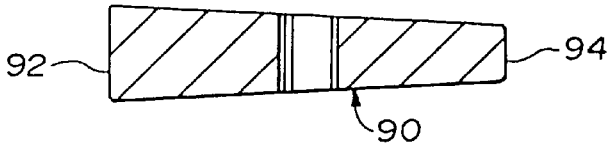
FIG. 12 is a cross-sectional view of the wedge of FIG. 10 through line 12—12.
Figure 13:
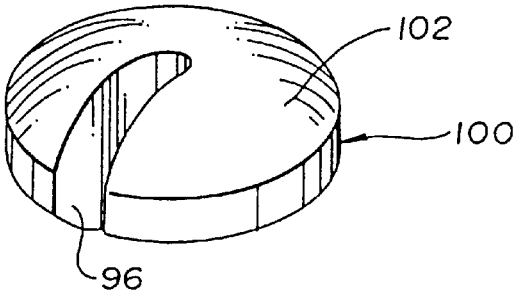
FIG. 13 is an alternative wedge in which a top is not planar.

The wedge 100 of FIG. 12 includes a similarly formed body, includes a slot 96 but no directional wedge. Rather, a surface 102 of wedge 100 is rounded or otherwise non-planar. In this manner, wedge 100 with surface 102 against a vertebra may allow rotational or angular correction of deformity. Wedges 100 may be inserted to replace the disc, forming a clamshell appearance in which both adjacent vertebrae would rest against a rounded surface 102.

Figure 14:
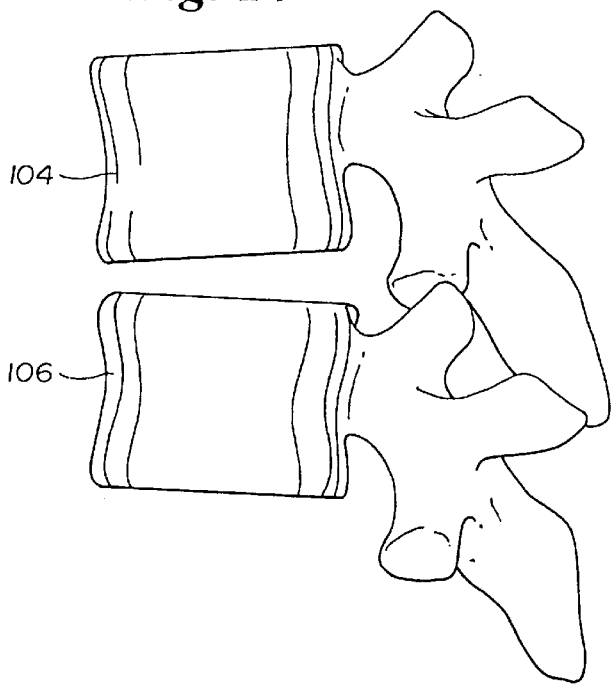
FIG. 14 shows a section of a spinal column in need of realignment.
Figure 15:
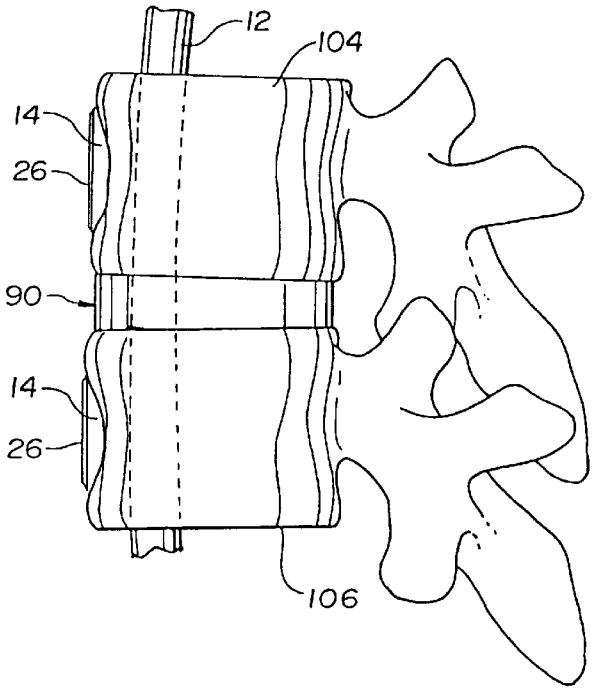
FIG. 15 shows the spinal column of FIG. 14 with a correcting wedge in place.

FIGS. 14 through 17 show how a wedge of the invention may be used to correct a defect of the spinal alignment. In FIGS. 14 and 15, a spinal column consisting of vertebra 104, 106 is out of alignment with the spine pitched forwardly. In FIG. 15 each vertebra includes a screw 14, rod 12 and a wedge 90 which, by virtue of its greater anterior height, corrects the alignment. This procedure may be used instead of bending rod 12 to obtain similar results, or in conjunction with a bent rod.

Figure 16:
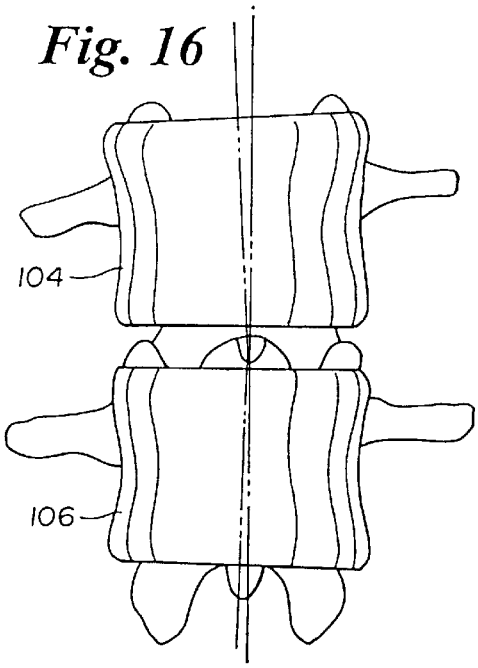
FIG. 16 shows a spinal column in need of alignment, such as in scoliosis.
Figure 17:
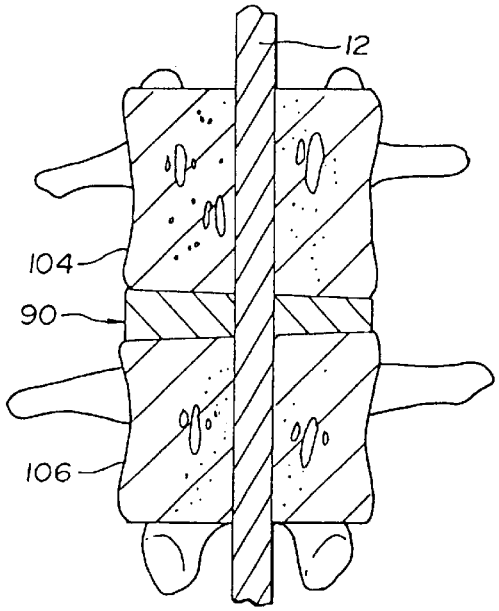
FIG. 17 shows the spinal column of FIG. 16 in cross-section, realigned with a correcting wedge.

FIGS. 16 and 17 show a typical scoliosis of the spine in which a corrective wedge 90 is slipped in from the side such that the thickest portion of the wedge 90 is to a side, thereby correcting the curvature. In all cases, the wedge is inserted into position, the vertebrae are allowed to contact the wedge and the locking caps 26 are screwed into engage with the rod 12 and keep the entire structure as desired.

The invention may be used anteriorly, anterior-laterally and laterally depending on the needs of the patient. The drawings show the anterior use of the bone screws as one possible position.

While this invention may embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A surgically implantable system for correction of a spiral abnormality which comprises:

(a) a rod adapted to extend within vertebrae of a spinal section in need of correction;

(b) at least two substantially hollow cylindrical members *each having an interior and an exterior surface and* each having a series of bone-engaging threads on the exterior surface of the cylindrical members, each of said cylindrical members including an upper [an] *and* a lower rim, *said upper rim having a diameter equal to or greater than a diameter of said lower rim,* each of said upper rims including a pair *of* opposing rod fixation slots to receive said rod transversely across said rim and to be below the plane of said rim, said rod being received in each rod fixation slot of each cylindrical member; and (c) a locking cap secured to each of said cylindrical members at said upper rims to thereby lock said rod to each said cylindrical member.

2. The surgically implantable system of claim 1 wherein said cylindrical members include threads and said locking caps include threads to engage with said cylindrical member threads to lock said caps to said cylindrical members.

3. The surgically implantable system of claim 1 wherein said rod is constructed and arranged such that its cross-section is not round.

4. The surgically implantable system of claim 3 wherein said rod includes a plurality of spaced dimples and said locking cap includes a projection which may interlock with one of said dimples to more securely lock said rod to said cylindrical member and cap.

5. The surgically implantable system of claim 3 wherein said rod includes a plurality of spaced projections and said locking cap includes a dimple which may interlock with one of said projections to more securely lock said rod to said cylindrical member and cap.

6. The surgically implantable system of claim 1 wherein said rod has a generally elliptical cross-section.

7. A spinal fixation system for fixing vertebrae comprising:

(a) at least two hollow threaded screws constructed to be positionable within a recessed ring cut into vertebrae anteriorally, anterolaterally or laterally, each of said screws having an exterior and interior surface and an upper and lower rim, said screws further including bone engaging threads on the exterior surface and opposing rod fixation slots extending from said upper rim;

(b) a rod of a length sufficient to span the distance between and connect each of said hollow threaded screws, said rod being inserted within the rod fixation slots of said screws; and (c) a locking cap secured to each of said screws at said upper rims to thereby lock said rod to each of said screws within the rod fixation slots.

8. A method for installing a spinal fixation system comprising the steps of:

(a) forming an annular cut into each vertebra to be joined together on the anterior, anterolateral or lateral surface of each vertebra;

(b) forming a channel between each of said vertebra having an annular cut;

(c) threading a threaded hollow screw into each annular cut, each of said screws including an upper rim having opposing rod fixation slots extending from said rim into said screw;

(d) positioning a single rod into each rod fixation slot of said screws and into said vertebral channels to thereby connect each screw with said rod, with said rod being at least substantially below the plane of said vertebral surfaces; and (e) locking said rod to each of said screws by positioning a locking cap to said upper rims of said screws, thereby capturing said rod thereto.

9. The method of claim 8 further including the step of placing a spinal alignment correcting wedge between at least one adjacent pair of vertebrae and around said rod to correct the spinal alignment.

10. A method for resecting a major portion of a vertebra and stabilizing the spine after resection comprising the steps of:

(a) surgically resecting the portion of bone of a vertebra which must be removed due to disease, tumor or fracture as required thereby leaving a gap between adjacent vertebrae;

(b) forming an annular cut into said adjacent vertebrae to be joined together on the anterior, anterolateral or lateral surface of each vertebra;

(c) forming a channel between each of said vertebra having an annular cut;

(d) threading a threaded hollow screw into each annular cut, each of said screws including an upper rim having opposing rod fixation slots extending from said rim into said screw;

(e) placing a corpectomy block into the gap between said adjacent vertebrae, said corpectomy block having end plates constructed and arranged to fit between said adjacent vertebrae and to allow bone ingrowth into said end plates to facilitate fusion of said adjacent vertebrae to said corpectomy block, said corpectomy block further including a channel;

(f) positioning a single rod into each rod fixation slot of said screws and into said vertebral channels and said corpectomy block channel to thereby connect each screw with said rod, with said rod being at least substantially below the plane of said vertebral surfaces;

(g) locking said rod to each of said screws by positioning a locking cap to said upper rims of said screws, thereby capturing said rod thereto.

*11. A surgically implantable system for correction of a spinal abnormality which comprises:*

*(a) a rod adapted to extend within vertebrae of a spinal section in need of correction;*

*(b) at least two substantially hollow cylindrical members each having an interior and an exterior surface and each having a series of bone-engaging threads on the exterior surface of the cylindrical members, each of said cylindrical members including an upper an a lower rim, said upper rim having a diameter equal to or greater than a diameter of said lower rim, each of said upper rims including at least one rod fixation slot to receive said rod transversely across said rim and to be below the plane of said rim, said rod being received in each rod fixation slot of each cylindrical member; and*

*(c) a locking cap secured to each of said cylindrical members at said upper rims to thereby lock said rod to each said cylindrical member.*

*12. A spinal fixation system for fixing vertebrae comprising:*

*(a) at least two hollow threaded screws constructed to be positionable within a recessed ring cut into vertebrae*

*anteriorally, anterolaterally or laterally, each of said screws having an exterior and interior surface and an upper and lower rim, said screws further including bone engaging threads on the exterior surface and at least one rod fixation slot extending from said upper rim;*

(*b*) *a rod of a length sufficient to span the distance between and connect each of said hollow threaded screws, said rod being inserted within the rod fixation slots of said screws; and*

(*c*) *a locking cap secured to each of said screws at said upper rims to thereby lock said rod to each of said screws within the rod fixation slots.*

*13. A method for installing a spinal fixation system comprising the steps of:*

(*a*) *forming an annular cut into each vertebra to be joined together on the anterior, anterolateral or lateral surface of each vertebra;*

(*b*) *forming a channel between each of said vertebra having an annular cut;*

(*c*) *threading a threaded hollow screw into each annular cut, each of said screws including an upper rim having at least one rod fixation slot extending from said rim into said screw;*

(*d*) *positioning a single rod into each rod fixation slot of said screws and into said vertebral channels to thereby connect each screw with said rod, with said rod being at least substantially below the plane of said vertebral surfaces; and*

(*e*) *locking said rod to each of said screws by positioning a locking cap to said upper rims of said screws, thereby capturing said rod thereto.*

*14. A method for resecting a major portion of a vertebra and stabilizing the spine after resection comprising the steps of:*

(*a*) *surgically resecting the portion of bone of a vertebra which must be removed due to disease, tumor or fracture as required thereby leaving a gap between adjacent vertebrae;*

(*b*) *forming an annular cut into said adjacent vertebrae to be joined together on the anterior, anterolateral or lateral surface of each vertebra;*

(*c*) *forming a channel between each of said vertebra having an annular cut;*

(*d*) *threading a threaded hollow screw into each annular cut, each of said screws including an upper rim having at least one rod fixation slot extending from said rim into said screw;*

(*e*) *placing a corpectomy block into the gap between said adjacent vertebrae, said corpectomy block having end plates constructed and arranged to fit between said adjacent vertebrae and to allow bone ingrowth into said end plates to facilitate fusion of said adjacent vertebrae to said corpectomy block, said corpectomy block further including a channel;*

(*f*) *positioning a single rod into each rod fixation slot of said screws and into said vertebral channels and said corpectomy block channel to thereby connect each screw with said rod, with said rod being at least substantially below the plane of said vertebral surfaces;*

(*g*) *locking said rod to each of said screws by positioning a locking cap to said upper rims of said screws, thereby capturing said rod thereto.*

* * * * *